(12) United States Patent
Rapp et al.

(10) Patent No.: US 6,548,095 B1
(45) Date of Patent: Apr. 15, 2003

(54) SUGAR-FREE COMPRESSED PRODUCTS

(75) Inventors: Knut M. Rapp, Offstein (DE); Ingrid Willibald-Ettle, Landau (DE)

(73) Assignee: Südzucker Aktiengesellschaft (DE)

( * ) Notice: Subject to any disclaimer, the term of this patent is extended or adjusted under 35 U.S.C. 154(b) by 36 days.

(21) Appl. No.: 09/613,481

(22) Filed: Jul. 11, 2000

Related U.S. Application Data

(62) Division of application No. 09/030,295, filed as application No. PCT/EP96/03740 on Aug. 24, 1996, now abandoned.

(51) Int. Cl.⁷ .............................................. A23L 1/236
(52) U.S. Cl. .................................................... 426/548
(58) Field of Search ................................ 426/548, 103, 426/567, 3, 5

(56) References Cited

U.S. PATENT DOCUMENTS

| | | | |
|---|---|---|---|
| 4,233,439 A | | 11/1980 | Schiweck et al. .......... 536/18.5 |
| 5,578,339 A | * | 11/1996 | Kunz et al. ................. 426/658 |

FOREIGN PATENT DOCUMENTS

| | | | |
|---|---|---|---|
| JP | 04121162 A | * | 4/1992 |
| WO | 95/07622 | * | 3/1995 |

OTHER PUBLICATIONS

"Palatinit®—Herstellung, technologische Eigenschaften und Analytik palatinithaltiger Lebensmittel*"; H. Schiweck; Rohstoffe Matieres premieres; Alimenta 19; 5–16(1980).

"Hydrogenation of D–Fructose and D–Fructose/D–Glucose Mixtures*"; M. Makkee, et al.; Carbohydrate Research, 138 (1985) 225–236; Elsevier Science Publishers B.V., Amsterdam—Printed in The Netherlands.

* cited by examiner

*Primary Examiner*—Arthur L. Corbin
(74) *Attorney, Agent, or Firm*—Ostrolenk, Faber, Gerb & Soffen, LLP

(57) ABSTRACT

The invention concerns improved sugar-free products, their production and use, in particular, coated products, their production and use. The products are characterized by their content in enriched mixtures of 1-O-α-D-glucopyranosyl-D-mannitol (1,1-GPM) and 6-O-α-D-glucopyranosyl-D-sorbitol (1,6-GPS).

4 Claims, 10 Drawing Sheets

SOLUBILITY OF ISOMALT® IN WATER (g/100 g SOLUTION)

| TEMPERATURE (°C) | ISOMALT® |
|---|---|
| 0 | 8.5 |
| 2 | 10.1 |
| 4 | 11.7 |
| 6 | 13.3 |
| 8 | 14.9 |
| 10 | 16.5 |
| 12 | 18.1 |
| 14 | 19.7 |
| 16 | 21.3 |
| 18 | 22.9 |
| 20 | 24.5 |
| 22 | 26.0 |
| 24 | 27.6 |
| 26 | 29.2 |
| 28 | 30.8 |
| 30 | 32.4 |
| 32 | 34.0 |
| 34 | 35.6 |
| 36 | 37.2 |
| 38 | 38.8 |
| 40 | 40.4 |
| 42 | 42.0 |
| 44 | 43.6 |
| 46 | 45.2 |
| 48 | 46.8 |
| 50 | 48.4 |
| 52 | 50.0 |
| 54 | 51.6 |
| 56 | 53.2 |
| 58 | 54.7 |
| 60 | 56.3 |
| 62 | 57.9 |
| 64 | 59.5 |
| 66 | 61.1 |
| 68 | 62.7 |
| 70 | 64.3 |
| 72 | 65.9 |
| 74 | 67.5 |
| 76 | 69.1 |
| 78 | 70.7 |
| 80 | 72.3 |

FIG. 6

SUGAR-FREE COMPRESSED PRODUCTS

This is a division of application Ser. No. 09/030,295, filed Feb. 25, 1998, now abandonded, which is a 371 of International Patent Application No. PCT/EP96/03740, filed Aug. 24, 1996.

BACKGROUND OF THE INVENTION

The invention under consideration concerns improved sugar-free products, their production and use, in particular, coated products, their production and use.

Coated products contain a coating produced from sugar, sugar alcohols, chocolates, and/or other glazes with a liquid, soft, or solid core. Chewing gum inserts, fruits, compressed material, or other pharmaceutical products are, for example, used as cores. Thus, for example, U.S. Pat. No. 4,792,453 describes a sugar-free coated chewing gum, whose coating contains hydrogenated isomaltulose. This chewing gum is obtained by coating with a syrup which contains the hydrogenated isomaltulose. Thus, 1-O-α-D-glucopyranosyl-D-mannitol (1,1-GPM) and 6-O-α-D-glucopyranosyl-D-sorbitol (1,6-GPS), dissolved in approximately equimolar quantities, are present in the syrup coating.

A number of methods for the production of coated products are also known. Essentially, a distinction is made between soft coating, hard coating, and suspension dragee formation. Soft coating means the application of saccharides dissolved in water on cores which are moving, wherein after each application, saccharide powder is sprinkled, so as to bind the moisture. This type of coating forms a soft dragée coating (European Patent No. 1,625,31 1 A1). The fact that the metering of the syrup used for the coating—that is, the dissolved saccharide—and the metering of the powder must be coordinated with one another proves to be a disadvantage, in addition to the complicated processing execution.

Hard coating is likewise understood to mean—just as with soft coating—the application of saccharides dissolved in water on cores which are moving, wherein, however, saccharide powder is not applied, but rather the nonaqueous components are immediately dried. As with soft coating, a large number of different individual applications (50–120) are carried out, between which drying is undertaken with warm or cold air, so that various thicknesses of dragée coatings can be produced. Also, hard coating methods with two different saccharide solutions, which are applied after one another ("dual-composition coating"), are also known. Thus, in more recent times, methods are described in which maltitol-containing layers are first applied and then the remaining coating was built up with xylitol (U.S. Pat. No. 5,376,389). These methods, however, use two different saccharides for the production of the solution to be applied and accordingly, have to be carried out in a complicated manner. In addition, coating layers made of xylitol detach readily during the coating process, in particular on the corners and edges of the coated cores.

Both in hard coating as well as in soft coating methods, the problem of the adhesion tendency upon application of the aqueous solutions arises—for example, when using hydrogenated isomaltulose for the coating. This adhesion tendency causes the coating material to stick together or a sticking to the walls of the container used for the coating.

A third possibility for coating is to be found in the use of a suspension. The suspended mixture used up to now—for the most part only with sugar-containing products—consists of a liquid phase (which, for example, contains sugar, rice starch, and glucose dissolved in water) and a solid phase which consists of fine, crystalline sugar particles. The separate use of various sucroses is characteristic of this type of suspension-coating.

The coating products obtained with the described methods tend to lose their crispiness during storage because of the composition of their coating and their core. The reason for this is apparently to be found in the diffusion of moisture from the core into the coating. In the long run, this process also leads to undesired drying out of the dragée core. Conversely, the known products exhibit an undesired water absorption in a moist warm atmosphere, whose results are sticky, soft products, which are thus unattractive for consumption.

Also the products which are not coated and have been known up to now in the state of the art are capable of improvement with regard to their storage capacity, sweetening power, or solubility. These disadvantages originate in the type and composition of the saccharides used for the production of the products or their mixtures, such as hydrogenated isomaltulose. Hydrogenated isomaltulose is formed by the hydrogenation of isomaltulose and contains the components 6-O-α-D-glucopyranosyl-D-sorbitol (below, referred to as 1,6-GPS) and 1-O-α-D-glucopyranosyl-D-mannitol (referred to below as 1,1-GPM) in a ratio of approximately 1:1. Hydrogenated isomaltulose is dissolved only moderately in water, and in dissolved form tends to adhere upon application to the surfaces involved in the coating.

SUMMARY OF THE INVENTION

The technical problem at the core of the invention under consideration thus is to make available products which overcome the aforementioned disadvantages, methods for their production, and their use.

The solution to this technical problem is to be found in making available the saccharide mixtures characterized in the patent claims, products containing these mixtures, methods for their production, and their use in the food area, in particular, the sweetener and pharmaceutical areas.

In particular, the invention makes available 1,6-GPS-enriched mixtures, consisting of 1,6-GPS and 1,1-GPM, in a ratio of 57:43 wt %, in particular greater than 57:less than 43 wt %, to 99:1 wt % (based on the dry substance of the mixture of 1,6-GPS and 1,1-GPM, used for production, wherein its 1,6-GPS/1,1-GPM content is equal to 100%) and 1,1-GPM-enriched mixtures, consisting of 1,6-GPS and 1,1-GPM, in a ratio of 1:99 wt % to 43 wt %:57 wt %, in particular, smaller than 43:greater than 57 wt % (based on the dry substance of the mixture of 1,6-GPS and 1,1-GPM, used for production, wherein its 1,6-GPS/1,1 -GPM content is equal to 100%). Depending on the composition of the starting substance used for their production, the mixtures can also contain small quantities of sorbitol, mannitol, etc. The mixtures in accordance with the invention can be used in a particularly advantageous manner in solution or as a suspension for the coating of products in the sweetener or pharmaceutical areas. In accordance with the invention, the mixtures can comprise an additive, an essential component, or essentially a sole component of the most varied products in the food or pharmaceutical areas. The 1,6-GPS- and 1,1-GPM-enriched mixtures in accordance with the invention can be, particularly advantageously, produced from a single basic substance, namely hydrogenated isomaltulose. Therefore, in accordance with the invention, it is possible to produce two mixtures, each with different characteristics, from this commercially obtainable basic substance. The 1,6-GPS-enriched mixture is characterized by an increased solubility and greater sweetening power, in comparison to hydrogenated isomaltulose and the 1,1-GPM-enriched mixture. The greater sweetening power is based, on the one hand, on the fact that 1,6-GPS goes into solution more rapidly and thus triggers a more rapid sweet sensation and, on the other hand, on the objectively greater sweetening power which is characteristic of the compound 1,6-GPS. The 1,1-GPM-enriched mixture exhibits a lower solubility than hydrogenated isomaltulose. The deliberate use of these two substances in products in the food, sweetener, or pharmaceutical areas makes it possible to impart to the products an improved storage stability and greater sweetening power and to simplify their production method.

The invention concerns, in particular, coated products, comprising a core and a coating, wherein the coating contains at least one layer made of a 1,6-GPS-enriched mixture, consisting of 1,6-GPS and 1,1-GPM, in a ratio of 57:43 wt %, in particular, greater than 57:smaller than 43 wt %, to 99:1 wt % (based on the dry substance of the mixture of 1,6-GPS and 1,1-GPM, used for production, wherein its 1,6-GPS/1,1-GPM content is equal to 100%) and/or of a 1,1-GPM-enriched mixture, consisting of 1,6-GPS and 1,1-GPM, in a ratio of 1:99 wt % to 43:57 wt %, in particular, smaller than 43:greater than 57 wt % (based on the dry substance of the mixture of 1,6-GPS and 1,1-GPM, used for production, wherein its 1,6-GPS/1,1-GPM content is equal to 100%). This/these layer(s) comprise(s) either exclusively—perhaps with the inclusion of impurities resulting from the starting substance, such as sorbitol or mannitol—the mixtures in accordance with the invention or the compositions containing the mixtures in accordance with the invention. The coated products, in accordance with the invention, contain either a core of known composition or a core which comprises one or two of the 1,6-GPS- or 1,1-GPM-enriched mixtures, in accordance with the invention, and a coating of at least one layer of one of the mixtures in accordance with the invention—that is, at least one layer of the 1,1-GPM- or 1,6-GPS-enriched mixture.

In a particularly preferred specific embodiment of the invention, the coated products exhibit at least one and preferably 25–45 layers of the 1,6-GPS- and 1,1-GPM-enriched mixture. The thus coated products are sheathed by layer sequences with different compositions. By selecting the series sequence and the number of coating steps with the various mixtures, it is possible to deliberately produce products with desired characteristics. In accordance with the invention, provisions can be made so that the core is first sheathed with, in total, 25–45 layers of the 1,1-GPM-enriched mixture and then on these layers, other, in particular 25–45, layers of the 1,6-GPS-enriched mixture are applied. Such a structured coated product is characterized, as a whole, by a higher sweetening power, in comparison to traditional products coated with hydrogenated isomaltulose, as a result of the higher solubility and greater sweetening power of the 1,6-GPS-enriched mixture forming the outer layers. Another advantage is found in the presence of the 1,1-GPM-enriched layer sequence between the core and outer layer, which prevents a diffusion of moisture to the surface of the dragée because of its lower solubility, in comparison to traditional hydrogenated isomaltulose. The products therefore exhibit an improved crispiness and longer storage stability. In addition and conversely, in the moist, warm atmosphere, less moisture penetrates from the surroundings into the core, so that the storage stability is improved even under these circumstances. The invention, however, also comprises an embodiment in which the layers close to the core are constituted from the 1,6-GPS-containing mixture, whereas the outer layer contains the 1,1-GPM-enriched mixture.

In the pharmaceutical field also, the solubility of products or, in the case of coated products, the solubility of their coatings, frequently plays a role. The solubility of the products or coatings directly influences the active-ingredient release and thus also the active site and the active time of the applied pharmaceuticals. In cases in which a more rapid release of the pharmaceuticals is desired, only, or predominantly, 1,6-GPS-enriched mixtures with their increased solubility are used, in accordance with the invention, as the coating or for the production of the drug carrier. Conversely, in cases in which a slower active-ingredient release is desired, only, or essentially, a 1,1-GPM-enriched mixture can be used for the production of the coating or the drug carrier.

The invention also concerns a method for the production of a coated product, which is characterized in that at least once a solution or suspension of the 1,6-GPS-enriched mixture and/or sometime before or subsequently, a solution or suspension of the 1,1-GPM-enriched mixture is applied on the core and the solvent is evaporated before the application of each layer. The method in accordance with the invention provides for either a solution or, particularly preferably, a suspension of one of the mixtures in accordance with the invention being applied at least once on a core. A multiple application is particularly preferred so that the coating comprises several layers. Particularly preferred is a method in which layers of the two mixtures in accordance with the invention are applied, one after another, on the core. A specific embodiment of the invention provides for 25–45 applications of the solution or suspension of the 1,1-GPM- and 1,6-GPS-enriched mixture to be carried out. Depending on the desired characteristics of the coated product, for example, the layers which contain the 1,1-GPM-enriched mixture are applied; they are then covered by 1,6-GPS-enriched layers. The invention, however, also comprises the application of 1,6-GPS-enriched layers first, followed by the application of 1,1-GPM-enriched layers. After the application of each layer, the solvent is evaporated, preferably with a gas flow which has a dew point of −15° to +10° C., with 0° C. being particularly preferable. The application of the suspension or solution is carried out while maintaining a constant temperature and while avoiding water losses. This can, for example, take place fully automatically in a DRIACOATER 1200 from the Driam Company, Eriskirch, wherein the suspension is sprayed on with a diameter of 1.5–2.0 mm, using Schlick fan nozzles.

DETAILED DESCRIPTION

In a preferred embodiment of the invention, the mixtures in accordance with the invention, in particular, the coating of the coated products containing these mixtures, also contain gum arabic in a quantity of 0.5–10 wt %, based on the dry substance of the coating. In accordance with the invention, the coating comprises 10–90 wt %, in particular, 25–35 wt % of the dry substance of the coated products. The mixtures in accordance with the invention and in particular, the coating of the coated products made from such mixtures can contain dyes, in particular, titanium dioxide.

In another specific embodiment of the invention, the mixtures and therefore also the coating have, moreover, one or more sugar substitutes, in particular, xylitol, mannitol, sorbitol, maltitol, lactitol, or erythritol. The invention also provides for the mixtures or the coating to also be able to contain fillers, in particular, polydextrose, calcium carbonate, or inulin.

The invention under consideration also comprises mixtures and coatings containing these mixtures, surfactant substances, such as polysorbates (ethoxylated sorbitan esters), in particular, in a quantity of 0.05–0.5 wt %, and/or film-forming agents, such as methylcellulose gelatin, hydroxypropyl cellulose, ethylcellulose, hydroxyethylcellulose, carboxymethylcellulose, and mixtures thereof. In addition, binders, such as alginates, plant gums, or plasticizers, can also be present.

In another specific embodiment, the invention concerns the mixtures in accordance with the invention and the mixture-containing coatings of coated products which contain intensive sweeteners, in particular, cyclamate, saccharin, aspartame, glycyrrhizin, dihydrochalcone, thaumatin, monellin, acesulfame, alitam, or sucralose.

In particular, the invention concerns a coated product, whose core is a chewing gum cushion, a chewing gum ball, a fruit, nut, bean-shaped chocolate, hard caramel, soft caramel, jelly, gum arabic product, nonpareil, small sugar bead, a snack, pharmaceutical product, or another lumpy food product.

The core can be of a known nature or contain a 1,6-GPS- or 1,1-GPM-enriched mixture of 1,6-GPS and 1,1-GPM. Of course, the invention can provide for this core to also contain the dyes, binders, sugar substitutes, intensive sweeteners, surfactants, or fillers. The invention also comprises a coated product with a core in the form of a compressed material. The compressed material can contain 1,6-GPS- or 1,1-GPM-enriched material or be a compressed material of the two mixtures. The selection and quantity of the mixture used for this compressed material in accordance with the invention influences its solubility and thus perhaps the pharmaceuticals contained in the compressed material also.

The invention also makes available a method for the production of a 1,6-GPS- and a 1,1-GPM-enriched 1,6-GPS- and 1,1-GPM-containing mixture of a single starting substance, namely hydrogenated isomaltulose, which is characterized in that hydrogenated isomaltulose is dissolved in water, crystalline hydrogenated isomaltulose is added in a quantity so that its solubility is exceeded, the formed suspension is filtered, and the 1,6-GPS-enriched filtrate is separated from the 1,1-GPM-enriched filter cake, or hydrogenated isomaltulose is mixed with water in such a ratio that the water quantity is not sufficient at the selected temperature so as to dissolve the entire quantity of isomalt mixture (see FIGS. 7 and 8).

Therefore, this method is characterized in that for the production of the two mixtures in accordance with the invention, merely one starting substance—namely, hydrogenated isomaltulose—is used. Hydrogenated isomaltulose can be obtained under the trade names Palatinit$^R$ or ISOMALT$^R$ from the Palatinit Company, Mannheim. It contains more than 98% 1,6-GPS and 1,1-GPM, wherein admixtures of sorbitol or mannitol are possible. In connection with the invention under consideration, concentrations of 1,6-GPS and 1,1-GPM always refer to the used quantity of 1,6-GPS and 1,1-GPM equal to 100%. In accordance with the invention, a saturated solution, for example, of ISOMALT$^R$ Type M, is produced at a temperature of 20°–95°. As a function of the temperature used, solid, powdery hydrogenated isomaltulose, for example, ISMOALT$^R$ Type PF (powder), is added at this temperature and this is done in such a quantity that the solubility described in FIG. 6 is exceeded by 1–40%. The crystalline, hydrogenated isomaltulose which is added to the aqueous solution of hydrogenated isomaltulose, therefore, experiences conditions under which a complete solution of the hydrogenated isomaltulose is no longer possible. A suspension is therefore formed. The total solids content of this suspension can thereby be approximately 50–90 wt %, wherein the solids are present partially dissolved and partially undissolved. In the production of the suspension, the mixture is preferably stirred well. The establishing of an equilibrium between the composition of the liquid and the solid phases of the suspension depends on the total solids fraction and the temperature and is completed after approximately 10–60 min. After the establishing of this equilibrium, a liquid phase is present which contains 1,6-GPS and 1,1-GPM in a ratio different from that in hydrogenated isomaltulose. The suspended, solid phase also contains 1,6-GPS and 1,1-GPM in a ratio different from that in hydrogenated isomaltulose. Moreover, 1,1-GPM is present in the solid phase in contrast to the 1,1-GPM in the liquid phase as a dihydrate. The composition of the liquid and the solid phases—that is, the quantitative ratios of 1,6-GPS to 1,1-GPM—can be adjusted in broad limits, in accordance with the invention—this can be done by means of the temperature of the suspension and the relatively undissolved solids fraction. FIGS. 1–5 illustrate that the composition of the phases obtained and thus of the mixtures in accordance with the invention can be regulated in a deliberate manner by adjusting the temperature and the relatively undissolved solids fraction. The total ratio (dissolved and solid) of 1,6-GPS to 1,1-GPM contained in the two phases corresponds, of course, to that of the used, hydrogenated isomaltulose. A low undissolved solids fraction in the suspension produces a high 1,1-GPM-dihydrate concentration in the solid phase, a high undissolved solids fraction, but a composition similar to that of the hydrogenated isomaltulose, wherein, however, 1,1-GPM-dihydrate is concentrated in the solid phase. In the solid phase, therefore, 1,1-GPM is always concentrated, wherein the ratio of 1,6-GPS to 1,1-GPM can vary from 1:99 wt % to 43:57 wt %, in particular smaller than 43:larger than 57 wt %. In the liquid phase, 1,6-GPS is always concentrated, wherein the ratio of 1,6-GPS to 1,1-GPM can vary from approximately 57:43 wt %, in particular, greater than 57:smaller than 43 wt %, to 99:1 wt %.

In accordance with the invention, the suspensions containing the two phases can also be produced by cooling supersaturated solutions of hydrogenated isomaltulose and a spontaneous or induced fine-grain formation, perhaps by the addition of inoculation crystals or ISMOALT$^R$ PF or PE.

After the equilibrium has been established by adjusting the temperature and the relatively undissolved solids fraction in the desired manner, the two phases are separated from one another in accordance with the invention. The separation of the two phases provided for in accordance with the invention takes place by filtering, centrifuging or sedimentation, but can also take place by means of other method steps. A 1,1-GPM-enriched solid phase and a 1,6-GPS-enriched liquid phase, each of which comprises 1,6-GPS and 1,1-GPM in different quantitative ratios, are obtained. The liquid phase can be converted into a solid phase by evaporating.

The method in accordance with the invention accordingly makes possible the preparation of 1,6-GPS-enriched mixtures, consisting of 1,6-GPS and 1,1-GPM, in a ratio of 57:43 wt %, in particular, greater than 57 wt % : smaller than 43 wt %, to 99:1 wt %. The invention also makes available 1,1-GPM-enriched mixtures, consisting of 1,6-GPS and 1,1-GPM, in a ratio of 1:99 wt % to 43:57 wt %, in particular, smaller than 43 wt %: greater than 57 wt %. These mixtures can, for example, be used in the form of their solution to make dragées. A suspension can also be used instead of a solution. The use of a suspension of hydrogenated isomaltulose and particularly preferred in accordance with the invention, a suspension of 1,6-GPS- or 1,1-GPM-enriched mixtures for the formation of coated products has the advantage of a strongly reduced adhesion tendency during the coating. Moreover, the application of highly dry substance contents in a relatively short drying time is possible, since undissolved solids, together with dissolved components, are applied on the dragee material. The advantageous, reduced adhesion tendency is based on the presence of very high fractions of crystallization nuclei, which consist of 1,1-GPM-dihydrate and 1,6-GPS.

The deliberate use of the different compositions and the related different characteristics of the mixtures in accordance with the invention permits not only the production of improved, glazed products or compressed materials, but of course, also the production of improved products in all areas in which sugar or sugar substitutes play a role. In accordance with the invention, for example, the 1,6-GPS-enriched mixture can be used as the soft filling in soft caramels. The 1,6-GPS-enriched mixture can also replace the previously used, very soluble sugar substitutes, such as maltitol, in the aforementioned products. Hard caramels can, in accordance with the invention be produced by using the 1,1-GPM-enriched mixtures. The products containing the mixtures in accordance with the invention, in particular, the glazed products or the coated products, can be composed by the suitable selection of the composition of the used mixtures and layer sequence so that the total composition of the 1,6-GPS and 1,1-GPM contained in the product corresponds to the composition in commercial hydrogenated isomaltulose (ISMOALT$^R$, Palatinit$^R$).

One specific embodiment of this invention makes available a product which comprises at least one of the mixtures enriched by 1,6-GPS and 1,1-GPM in accordance with the invention. These products can also contain gelatin, fat or fat substitutes. They can, of course, also contain the already mentioned fillers, binders, dyes, intensive sweeteners, emulsifiers, surfactants, sugar substitutes, other sweeteners, or pharmaceutical active ingredients.

The invention concerns, in particular, products which take the form of a hard caramel, soft caramel, gelatin product, chocolate, chocolate kiss, chewing gum cushion, chewing gum strip, foam sugar goods, baked goods, cookies, coated products or medication.

The mixtures in accordance with the invention can be polymerized in an advantageous manner with the monomers of known plastics, for example, polyurethane, and form addition polymers which can be used in the most varied areas, such as plastics technology or pharmacy.

In particular, the invention concerns a product which takes the form of a compressed material. In accordance with the invention, compressed materials can, for example, contain the compressed, solid 1,1-GPM-enriched phase of the mixture in accordance with the invention. A compressed material, in accordance with the invention, which contains the 1,6-GPS-enriched mixture obtained by evaporation from the liquid 1,6-GPS enriched phase, is also preferred. The compressed materials are particularly suitable for inclusion of drugs and their application. They can, for example, be in the form of tablets which are sucked or chewed.

The invention also provides for the production of the compressed materials from the two mixtures in accordance with the invention. Depending on the composition of the two individual mixtures and the relative fraction of these individual mixtures in the compressed material, it is possible to establish desired solubility characteristics in a controlled manner.

BRIEF DESCRIPTION OF THE FIGURES

The figures show the following:

FIG. 6 represents the solubility of hydrogenated isomaltulose (ISMOALT$^R$) in water.

EXAMPLES

Example 1

Production of 1,1-GPM- and 1,6-GPS-enriched 1,1-GPM/1,6-GPS Mixtures at 70° C. (with the Addition of Gum Arabic)

1920 g ISMOALT$^R$ Type M (hydrogenated isomaltulose) and 67.5 g gum arabic (rapidly soluble) are dissolved in 670.8 g water at 80° C. and subsequently cooled to 70° C. While stirring, 341.7 g ISMOALT$^R$ PF (powder) are added. The water content of 3.5 wt % in ISMOALT$^R$ was taken into consideration thereby.

After 60 min, the solid phase is separated from the liquid phase. This can occur, for example, by centrifugation or filtration.

In the example under consideration, the separation of the solid phase from the liquid phase is undertaken by filtration via a pressure filter tempered to 70° C. after 20, 60, 120, and 180 min. The compositions of the obtained phases are represented in Table I, below:

TABLE 1

| Sample | 1 | 2 | 3 | 4 |
|---|---|---|---|---|
| Filtrate in g | 85.85 | 100.89 | 130.83 | 100.9 |
| Filter cake (moist) | 37.76 | 51.55 | 54.76 | 32.34 |
| Filter cake (dry) | 34.30 | 48.56 | 52.10 | 29.53 |
| Filtrate (1,6-GPS:1,1-GPM) % | 75.1:24.9 | 76.7:23.3 | 77:23 | 74.5:25.5 |
| (1,6-GPS:1,1-GPM) % Solid | 61:39 | 66.5:33.5 | 67.6:32.4 | 67.2:32.8 |

Figure 1:
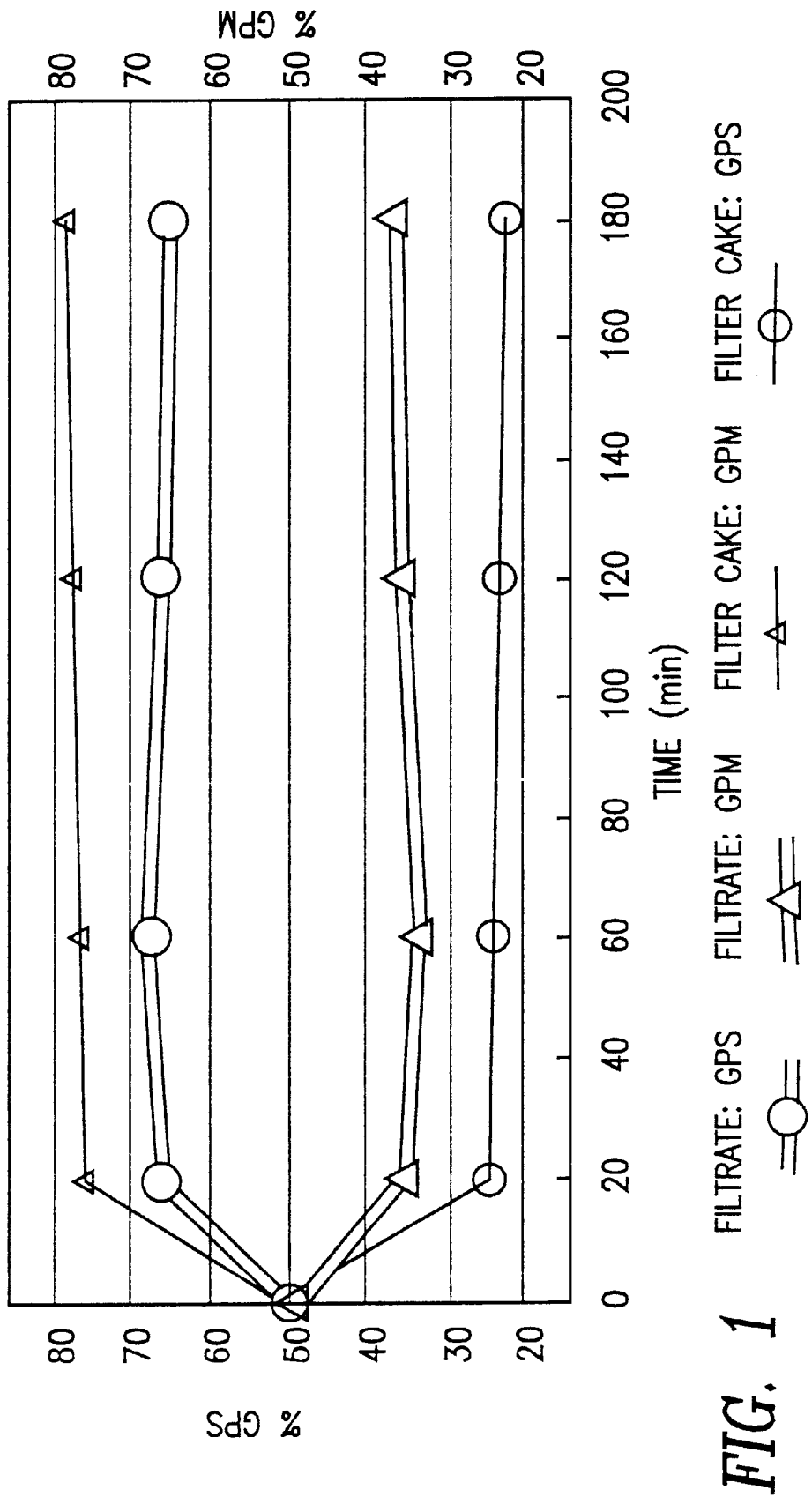
FIG. 1 represents the composition of the 1,6-GPS- and 1,1-GPM-enriched phases, which are obtained from a suspension, heated to 70° C., with a dry substance fraction of 75 wt %.
Figure 2:
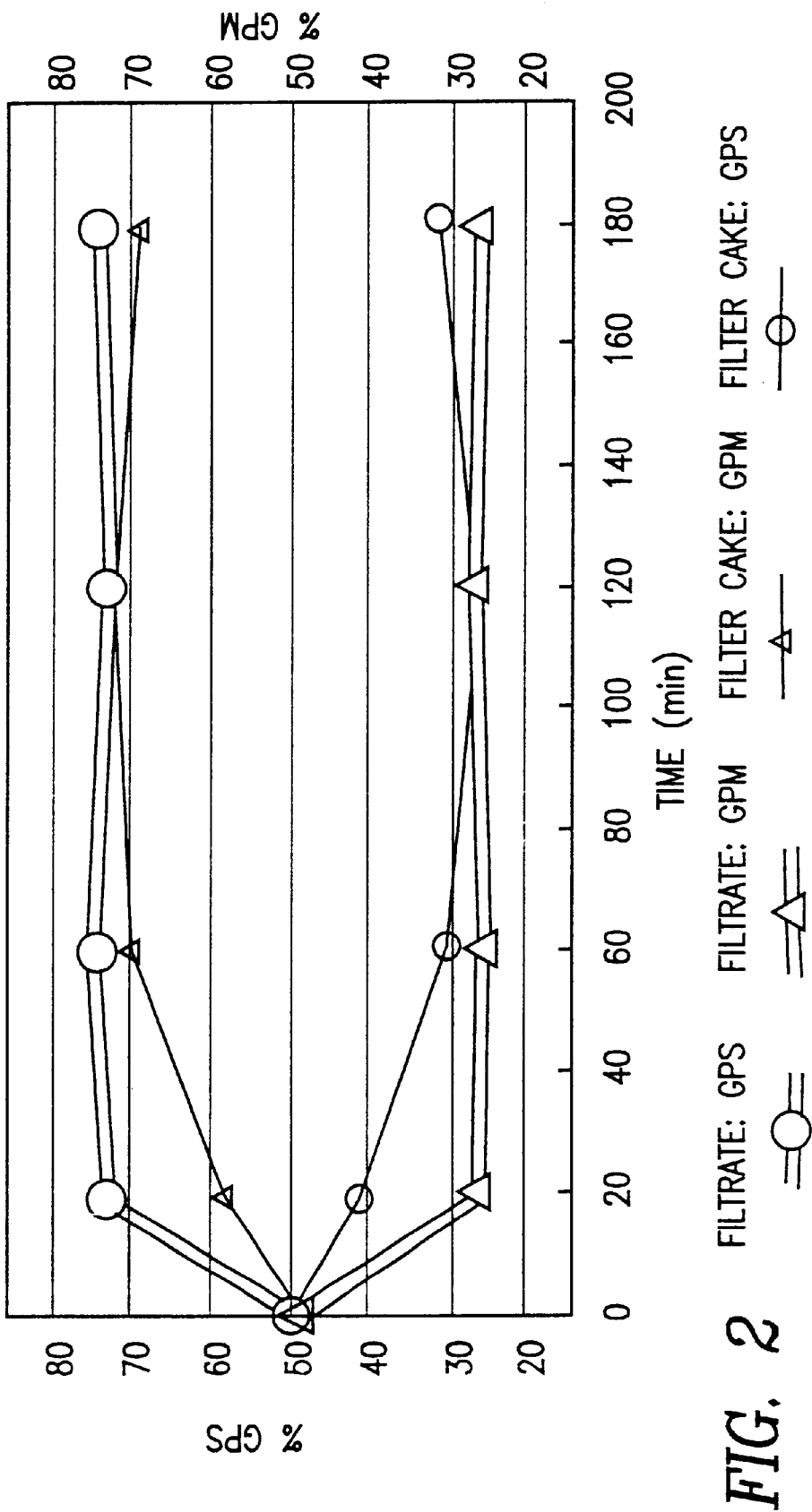
FIG. 2 represents the composition of the 1,6-GPS- and 1,1-GPM-enriched phases, which are obtained from a suspension, heated to 70° C., with a dry substance fraction of 80 wt %.
Figure 3:
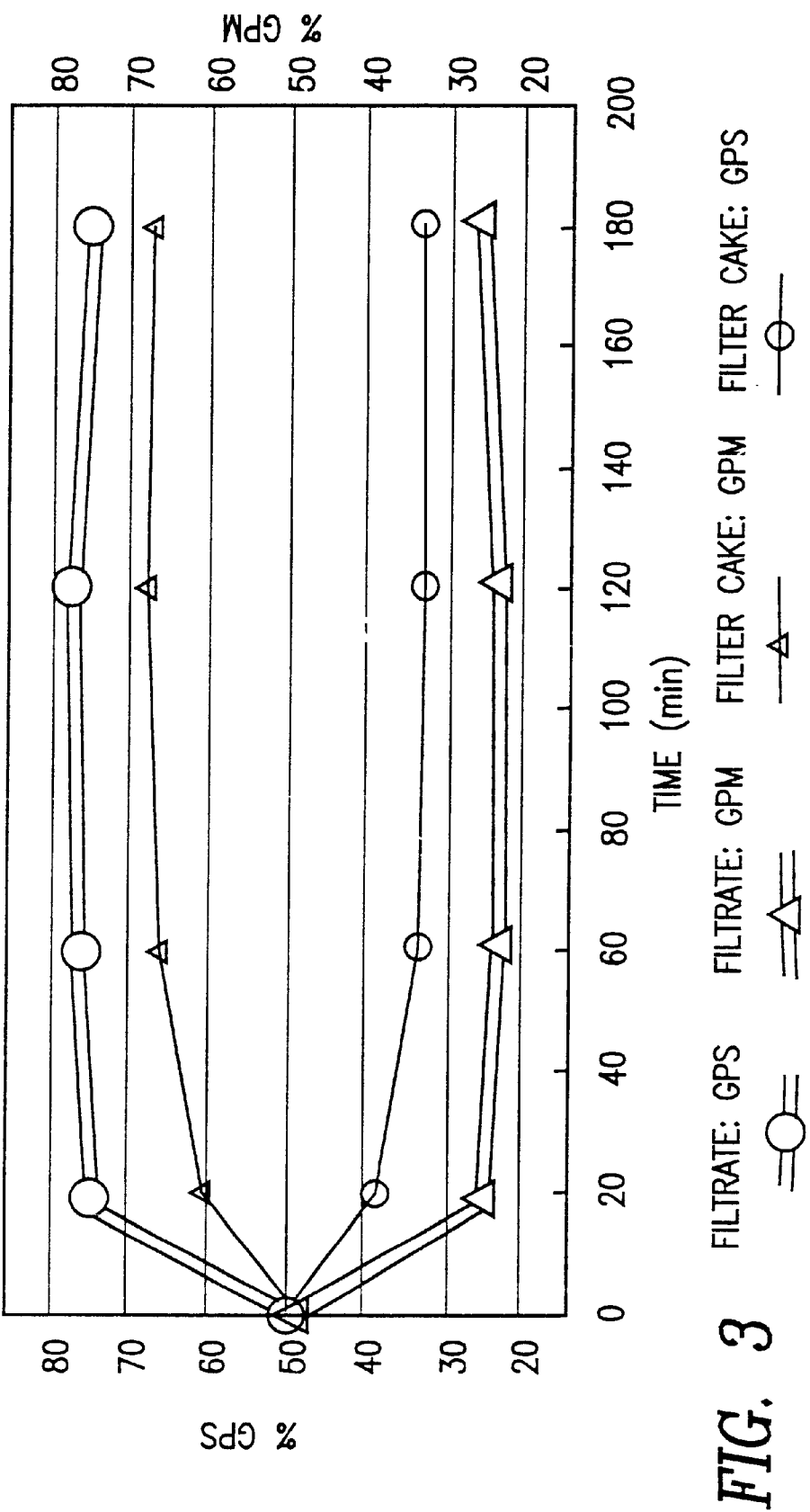
FIG. 3 represents the composition of the 1,6-GPS- and 1,1-GPM-enriched phases, which are obtained from a suspension, heated to 60° C., with a dry substance fraction of 75 wt %.
Figure 4:
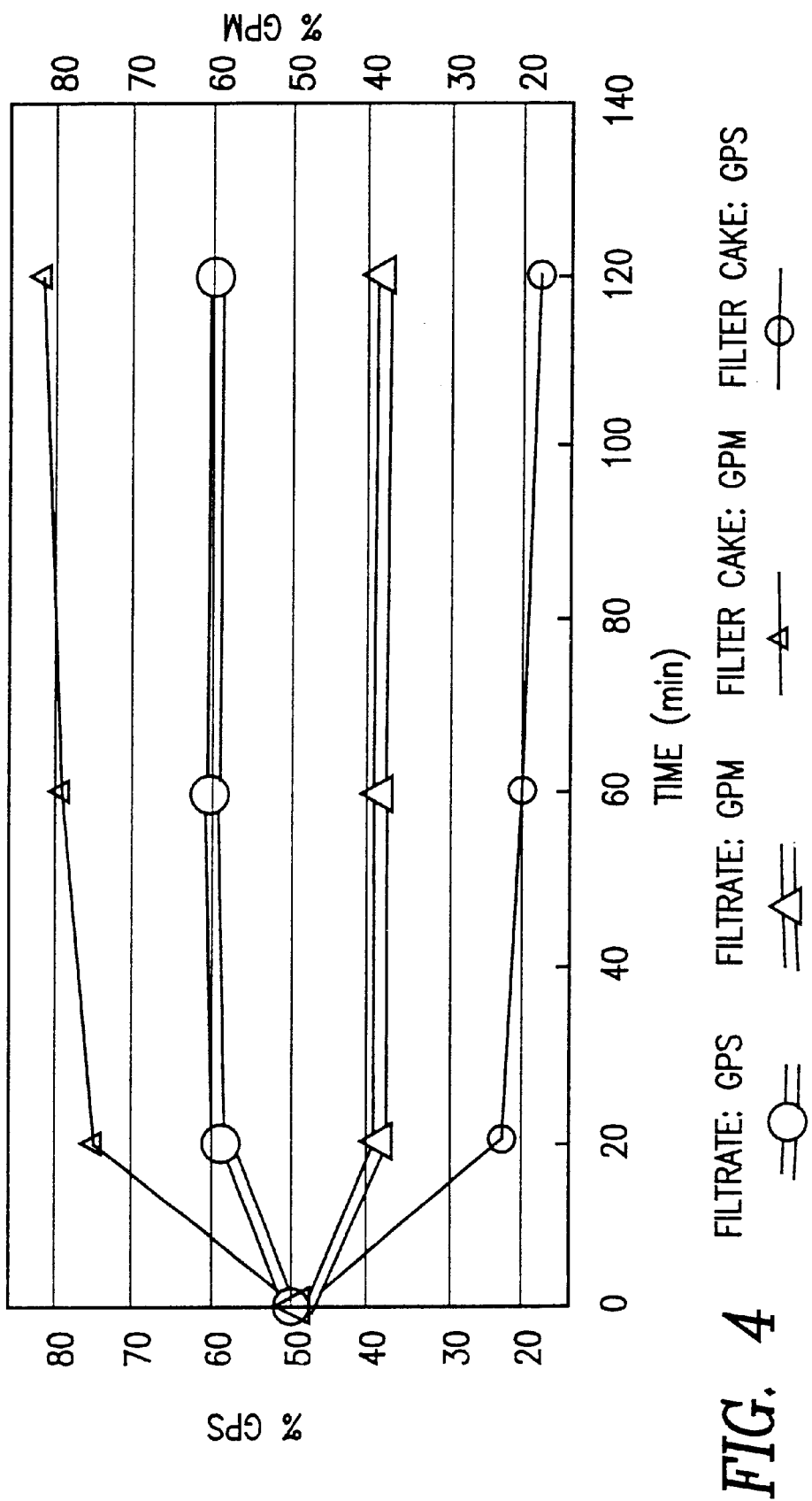
FIG. 4 represents the composition of the 1,6-GPS- and 1,1-GPM-enriched phases, which are obtained from a suspension, heated to 60° C., with a dry substance fraction of 65 wt %.
Figure 5:
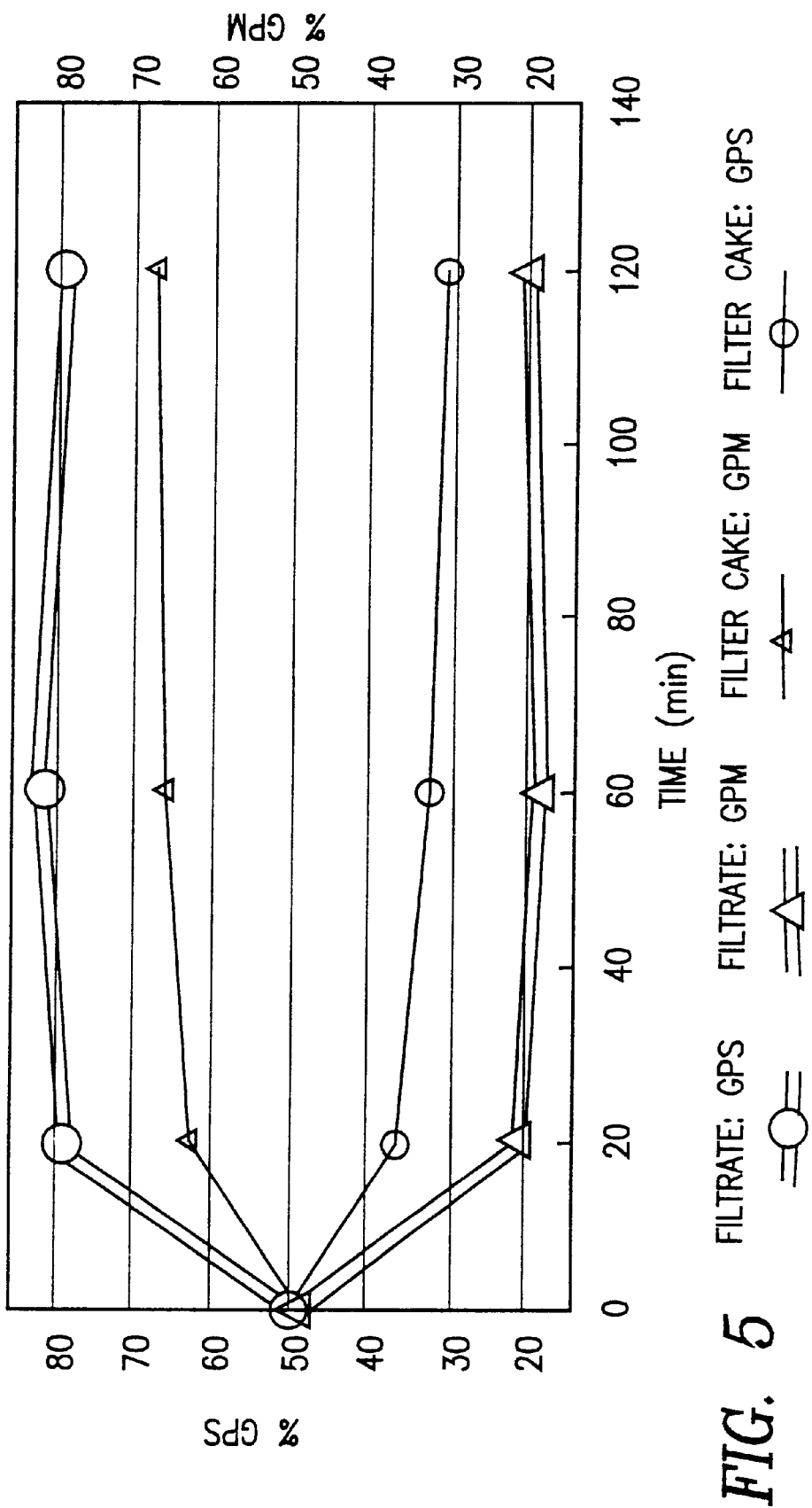
FIG. 5 represents the composition of the 1,6-GPS- and 1,1-GPM-enriched phases, which are obtained from a suspension, heated to 50° C., with a dry substance fraction of 70 wt %.

The results are shown in FIG. 1 in graphical form.

After 60 min, 1,6-GPS has been concentrated to approximately 75% in the liquid phase, whereas in the solid phase, 1,1-GPM (calculated without water of hydration) has been concentrated to more than 65%.

The liquid phase can be converted into suspension form or into the solid phase by evaporating or reducing the temperature.

By repeating this suspension-separation method with the individually obtained phases, 1,6-GPS or 1,1-GPM is obtained in pure form. It is also possible, in accordance with the invention, to obtain 1,1-GPM/1,6-GPS-enriched mixtures of a desired composition by the selection of suitable temperatures and concentrations of hydrogenated isomaltulose and perhaps a repetition of the separation process several times.

Example 2

Production of 1,1-GPM- and 1,6-GPS-enriched 1,1-GPM/1,6-GPS Mixtures at 35° C.

5 kg Isomalt$^R$ are added to 5 kg water (fully deionized). The suspension is stirred at 35° C. for 1–20 h, depending on the grain size.

Subsequently, this suspension is separated into the liquid and solid phases in a heated pressure filter at 35° C.

The clear solution is evaporated and dried in a rotary evaporator, perhaps subsequently comminuted.

1.95 kg white solid are obtained (water content before drying 24.8%, 1,1-GPM:1,6-GPS ratio 84:16%) and 7.86 kg clear solution (42.3° Brix, 1,1-GPM:1,6-GPS ratio 33.5:66.5%).

The separation of the two phases can take place also by means of a vacuum filter, centrifuge or by sedimentation.

Examples 1 and 2 and FIGS. 1–5 illustrate that with a deliberate use of the reaction parameters, temperature and solids concentration, it is possible to obtain mixtures of a desired composition.

Figure 7:
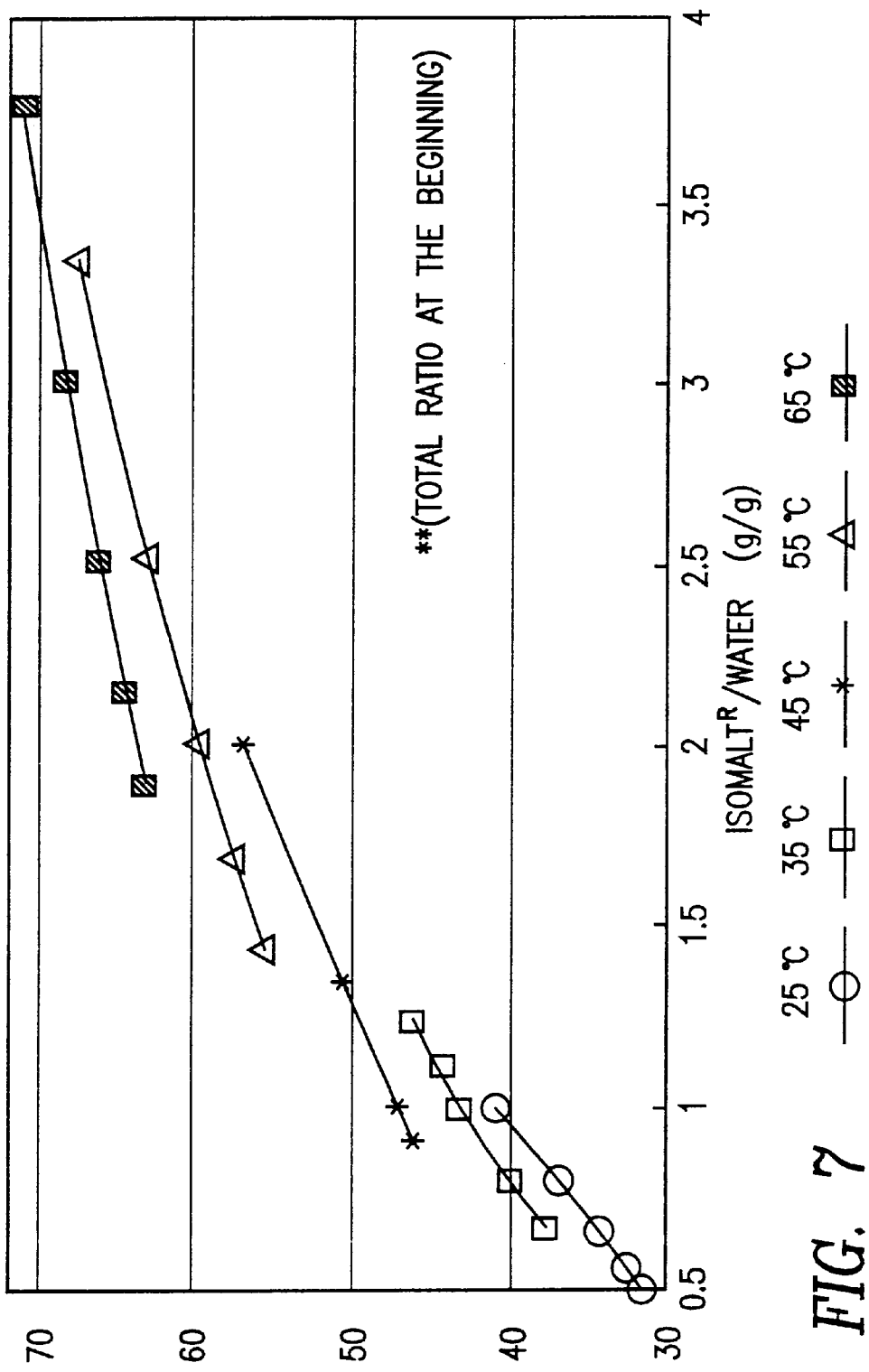
FIG. 7 represents the connection between the dry substance content (Bx value) of a solution saturated with hydrogenated isomaltulose (=ISMOALT$^R$) and the starting concentration of hydrogenated isomaltulose in water at different temperatures.
Figure 8:
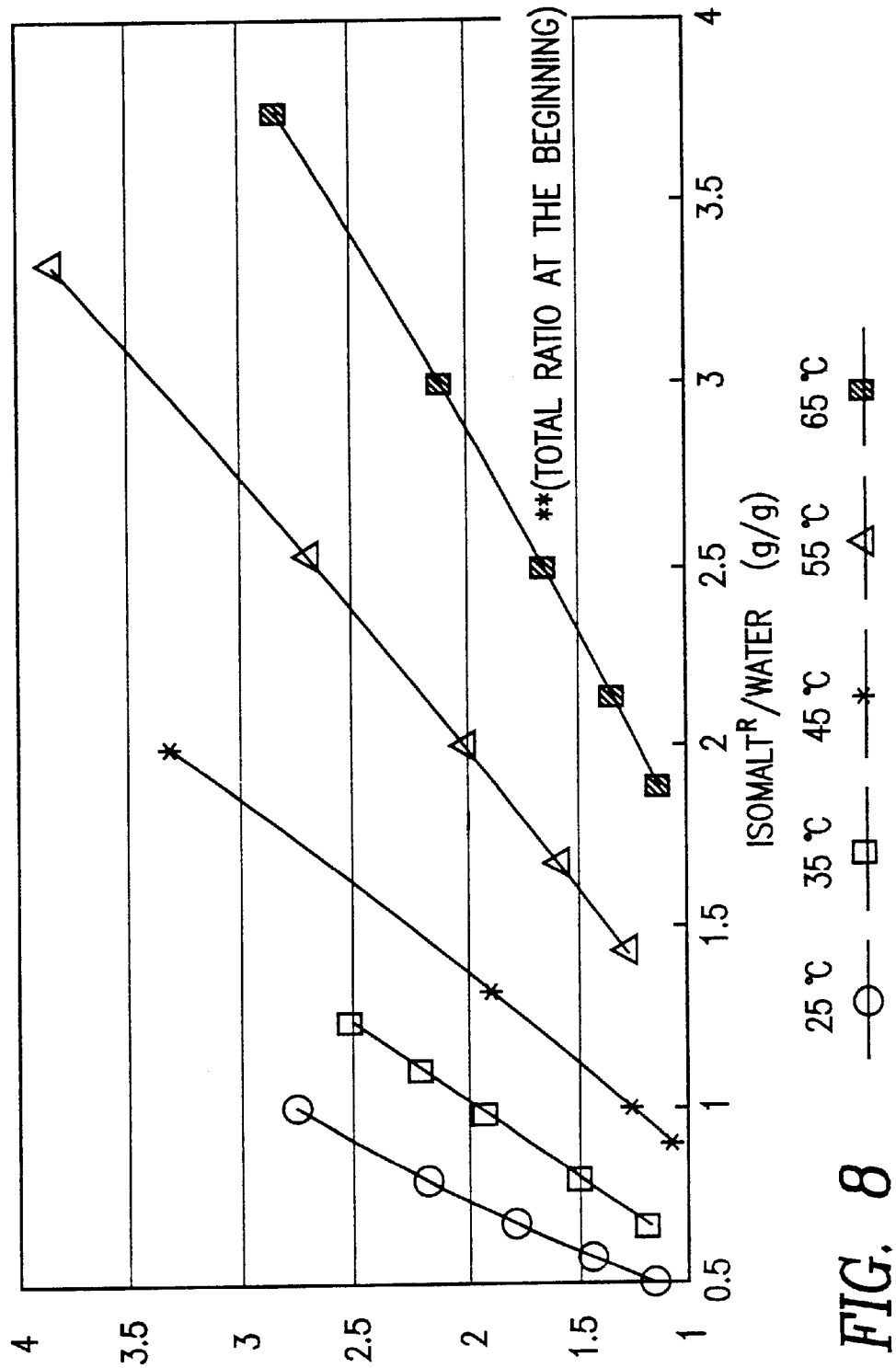
FIG. 8 represents the connection between the ratio of 1,6-GPS and 1,1-GPM in a solution saturated with hydrogenated isomaltulose and the starting concentration of hydrogenated isomaltulose in water at different temperatures.

FIGS. 7 and 8 illustrate this advantage in accordance with the invention.

From these figures one can see at what ratio hydrogenated isomaltulose (ISMOALT$^R$) is mixed with water and at what temperature this suspension must be maintained, so as to obtain a liquid phase with a certain 1,6-GPS:1,1-GPM ratio, for example.

If, for example, ISMOALT$^R$ is mixed with water at a ratio of 2:1, then an approximately 57° Brix solution with a 1,6-GPS:1,1-GPM ratio of 77:23%, i.e., 3,3:1 is obtained at a temperature of 45° C.

The same mixture, however, leads to an approximately 59° Brix solution with a 1,6-GPS:1,1-GPM ratio of 67:33%, i.e. 2:1, at 55° C.

Example 3

Production of Coated Products in the Hard Coating Process

Recipe:

| | |
|---|---|
| 1,1-GPM-enriched mixture (85% GPM, 15% GPS) | 30 kg |
| Gum arabic | 1.25 kg |
| Titanium dioxide | 0.5 kg |
| Water | 18.3 kg |

Production of the Coating Solution and the Coating Process

The 1,1-GPM-enriched mixture and gum arabic are dissolved in water at approximately 85° C., cooled to 70° C., and then titanium dioxide is suspended therein.

This mixture is maintained at 70° C., while stirring, and applied on chewing gum cushions (approximately 50–80 individual applications) in a hard coating process.

The chewing gum inserts (60 kg) are moved in a Diacoater 1200 (Driam Company, Eriskirch) and dried with air (temperature 25° C., dew point 0° C.) in a counterflow method after each application, for 2–5 min.

The advantage of the used sugar-free raw material (1,1-GPM-enriched mixture) is to be found particularly in the fact that due to the low solubility of the 1,1-GPM-dihydrate formed on the cores, a barrier layer is formed around the core, which prevents the diffusion of water and other volatile fractions (flavors) from the core. In this way, there is no drying out, as is frequently observed with other dragées. Also the sensorically determinable crispiness is maintained for a longer period of time.

Example 4

Production of Coated Products in the "Dual Composition" Process

Recipe I:

| | |
|---|---|
| 1,1-GPM-enriched mixture (85% 1,1-GPM, 15% 1,6-GPS) | 15 kg |
| Gum arabic | 0.6 kg |
| Titanium dioxide | 0.25 kg |
| Water | 9.5 kg |

Recipe II:

| | |
|---|---|
| 1,6-GPS-enriched mixture (77% 1,6-GPS, 23% 1,1-GPM) | 16 kg |
| Gum arabic | 0.6 kg |
| Titanium dioxide | 0.25 kg |
| Water | 7.75 kg |

Methods

Recipe I is produced as described in Example 3 and sprayed on the chewing gum inserts, wherein half of the dragee coating (layers directly on the core) is applied in 45 individual applications.

Recipe II is produced as in recipe I, wherein, however, the temperature of the mixture is 60° C. In 35 individual applications, this suspension is brought up to the desired dragée end weight on the chewing gum inserts coated with recipe I.

The experimental parameters correspond to those of Example 3.

The hard-to-dissolve 1,1-GPM-dihydrate from recipe I (see also Example 3) forms a barrier layer against moisture from the core. The 1,6-GPS-enriched outer layer influences the sweet sensation in a positive manner, as is shown by sensory investigations (threshold value determinations, differentiation testing in pairs).

Example 5

Production of Coated Products in the Suspension Method

Recipe

| | |
|---|---:|
| 1,6-GPS-enriched mixture (73% 1,6-GPS, 27% 1,1-GPM) | 43.6 kg |
| Water | 29 kg |
| Acesulfame K | 0.05 kg |
| Aspartame | 0.05 kg |
| Titanium dioxide | 1.0 kg |
| Gum arabic | 2.05 kg |
| 1,6-GPS-enriched mixture (powder, 77% 1,6-GPS, 23% 1,1-GPM) | 24.25 kg |

Production of the Suspension

While stirring, 1,6-GPS-enriched mixture (43.6 kg) and gum arabic are dissolved in water and the solution is heated to 75° C., until a crystal-free solution is present; this solution is cooled to approximately 60° C.; aspartame, acesulfame K, titanium dioxide, and 1,6-GPS-enriched mixture (powder) are added until a homogeneous mass is present. The temperature of the suspension is regulated to 55° C. and retained during the process.

The coatings are formed in a manner analogous to the method described under Example 3. A highly dry substance application per unit time is produced. Among other things, a more rapid sweet sensation during consumption is perceived by the increased solubility of 1,6-GPS.

Example 6

Production of Chewing Gum (Strips) Containing a 1,6-GPS-enriched and a 1,1-GPM-enriched 1,1-GPM/1,6-GPS Mixture Recipe

| | |
|---|---:|
| Chewing base Nostic TWA | 1.5 kg |
| 1,6-GPS-enriched mixture (76.5% 1,6-GPS, 23.5% 1,1-GPM) | 2.0 kg |
| Sorbitol syrup (70% dry substance) | 0.6 kg |
| 1,1-GPM-enriched mixture (85% 1,1-GPM, 15% 1,6-GPS) | 0.5 kg |
| Glycerol | 0.15 kg |
| Menthol | 0.15 kg |
| Flavor (Spearmint) | 0.1 kg |
| Aspartame | 2.5 g |
| Acesulfame K | 2.5 |

Production

The chewing gum base is heated at approximately 55° C. in a heating oven, before it is placed in a kneader; subsequently, the chewing gum base is kneaded for 1–2 min. During the kneading, the powdery additives (1,1-GPM- and 1,6-GPS-enriched mixture, sweetener, menthol) are gradually added in the indicated sequence; afterwards flavor, sorbitol syrup, and glycerol are added. The kneading continues until the mass is homogeneous (end temperature, approximately 45° C.). The mass is taken from the kneader and divided into portions which weigh approximately 1 kg.

The chewing gum mass divided into portions is placed in intermediate storage for approximately 15–20 min on a talc-strewn substrate, extruded with a suitable extruder, and further processed as usual.

The extensive replacement of the readily soluble sugar alcohol sorbitol and the complete replacement of the likewise readily soluble maltitol by the less-soluble sugar alcohols 1,6-GPS and 1,1-GPM leads to the so-called "long-lasting" effect (flavor reinforcement).

The product is particularly suitable for diabetics also.

Example 7

Production of Soft Caramels (Fruit Flavor) Containing a 1,6-GPS-enriched and a 1,1-GPM-enriched 1,1-GPM/1,6-GPS Mixture Recipe

| | |
|---|---:|
| 1,6-GPS-enriched mixture (67% 1,6-GPS, 33% 1,1-GPM) | 24 kg |
| Raftilose L95 (80% dry substance, fructooligosaccharide) | 51 kg |
| Water | 5 kg |
| Gelatin 120 Bloom (40%) | 3.6 kg |
| Vegetable fat (34–36° Sp) | 6.0 kg |
| Emulsifier | 0.8 kg |
| Citric acid (monohydrate) | 0.7 kg |
| 1,1-GPM-enriched mixture (85% 1,1-GPM, 15% 1,6-GPS) | 8 kg |
| Flavor (lemon) | 0.1 kg |

Production

The 1,6-GPS-enriched mixture, Raftilose L95, and water are boiled in a batch boiler to 132–136° C.(depending on the desired consistency); the gelatin solution, vegetable fat, emulsifier, citric acid, and 1,1-GPM-enriched mixture are added in the indicated sequence and mixed at a high speed for 2–3 min, until a homogeneous mass is formed. Finally, flavor is added and the vessel is emptied. Homogenizing with a suitable homogenizer (Homozenta) is advantageous. The soft caramel mass, cooled to 44–46° C., is then drawn for 5–10 min (temperature is then 47–49° C.).

In contrast to the common sugar-free soft caramels, the product produced above contains only diabetic-suitable additives.

Example 8

Production of Hard Containing a 1,1-GPM-enriched 1,1-GPM/1,6-GPS Mixture

Recipe

| | |
|---|---:|
| 1,1-GPM-enriched mixture (85% 1,1-GPM, 15% 1,6-GPS) | 25 kg |
| Water | 8 kg |
| Citric acid | 0.3 kg |
| Flavor (pineapple) | 0.1 kg |
| Acesulfame K | 25 g |

Production

The 1,1-GPM-enriched mixture and water are boiled in a candy boiler to 155–160, exposed to a full vacuum for 5 min, and after cooling the mass to 110–115° C., acid, flavor, and sweetener are added. Subsequently, the mass is given the shape of candies and cooled.

Alternately, the recipe above can be processed directly to candies, without the addition of water, in a melt extrusion process. The melt extrusion process can, of course, also be used if hard caramels are produced from the 1,6-GPS-enriched mixture.

1,1-GPM-enriched hard caramels form a microcrystalline boundary layer of 1,1-GPM-dihydrate on the surface, which leads to a reduced stickiness and reduces the further water intake from the atmosphere (favorable storage behavior). The products are suitable for diabetics.

Moreover, 1,1-GPM-enriched hard caramels exhibit an increased temperature stability. The temperature stability is described by the glass-transition temperature Tg° C.—that is, 1,1-GPM-enriched hard caramels have a high glass-transition temperature (Tg=65.6° C.+/−1.8° C., in comparison to IsomaltR hard caramels Tg=57.5° C.+/−1.7° C.).

Example 9

Production of a Compressed Material of 1,1 -GPM- and 1,6-GPS-enriched 1,1-GPM/1,6-GPS Mixtures Recipe

|   |   | Fruit flavor | Mint flavor |
|---|---|---|---|
| a) | 1,1-GPM-enriched mixture (85% 1,1-GPM, 15% 1,6-GPS) | 9.9 kg | 9.9 kg |
| b) | 1,6-GPS-enriched mixture (83% 1,6-GPS, 17% 1,1-GPM) | 9.9 kg | 9.9 kg |
|   | Acesulfame K | 15 g | 15 g |
|   | Citric acid | 30 g | — |
|   | Flavor | 50 g | 50 g |
|   | Magnesium stearate | 50 g | 50 g |

Production of tablets for sucking (tablets for chewing)

The components are mixed and pressed in an eccentric press under the following conditions:

| Force of pressure | 20–70 kN |
|---|---|
| Specific force of pressure | 0.2–0.9 kN/mm$^2$ |

For tablets for sucking, a) 1,1-GPM-enriched mixture is used; b) 1,6-GPS-enriched mixture is used for tablets for chewing.

Figure 9:
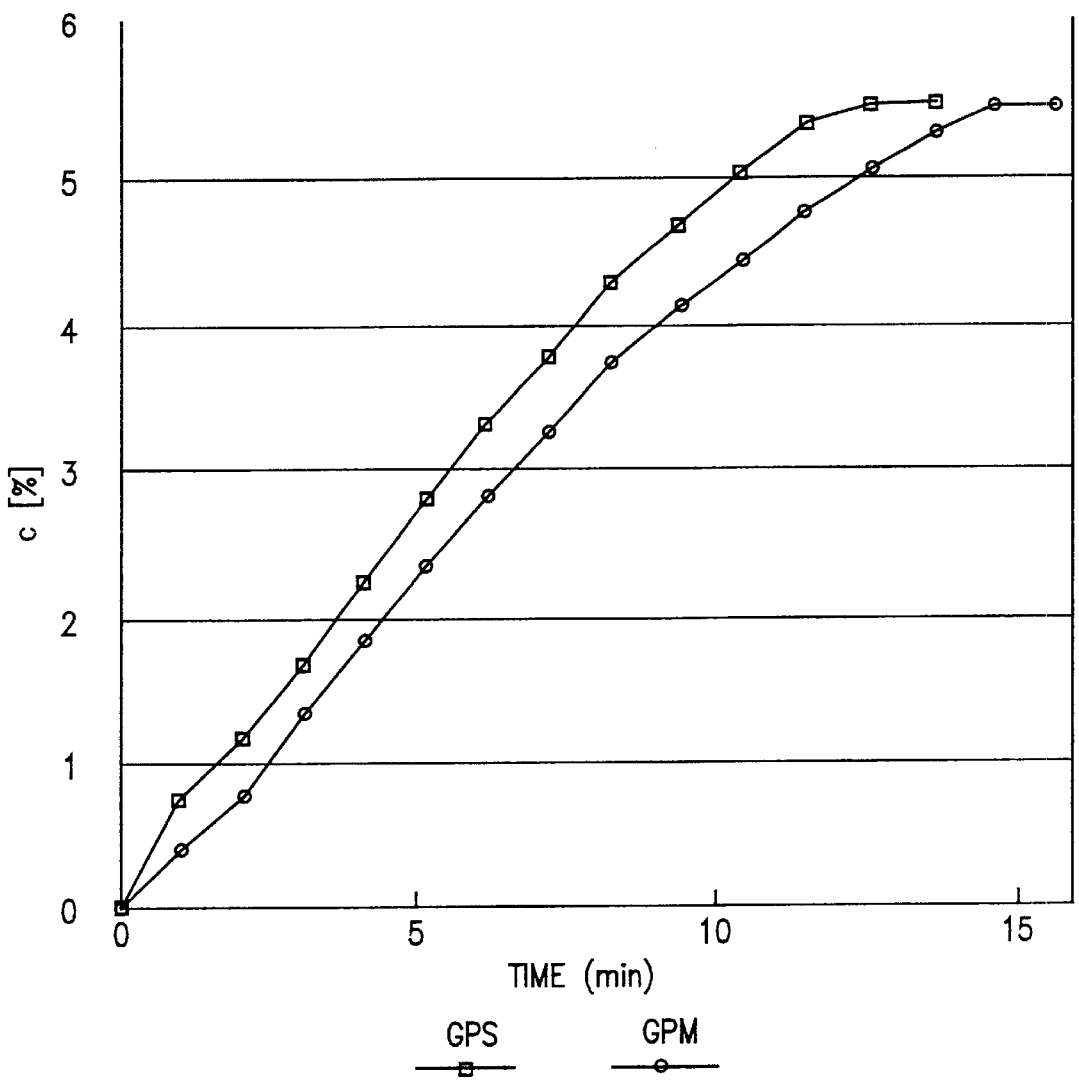
FIG. 9 represents the dissolution kinetics of compressed materials consisting of 1,6-GPS and 1,1-GPM.

A slow dissolution and thus a prolonged release of flavor or active ingredients with compressed pharmaceutical materials is brought about as a result of the low solubility of the 1,1-GPM-enriched mixture. FIG. 9 illustrates the lower solubility of a 1,1-GPM-enriched compressed material in comparison to a 1,6-GPS-enriched compressed material. The 1,6-GPS-enriched compressed materials were compressed without auxiliaries under 70 kN; the 1,1-GPM-enriched compressed materials, under 50 kN, also without auxiliaries.

Example 10

Production of Filled Hard Caramels, wherein the Shell of the 1,1-GPM-enriched Mixture and the Liquid Filling Contain 1,6-GPS-enriched Mixture 1. Hard Caramel Mass

| 1,1-GPM-enriched mixture (85% 1,1-GPM, 15% 1,6-GPS) | 25 kg |
|---|---|
| Water | 8 kg |
| Citric acid | 0.3 kg |
| Lemon flavor | 0.03 kg |

Production

The 1,1-GPM-enriched mixture and water are boiled in a candy boiler at 155–160° C., exposed to a full vacuum for 5 min, and subsequently, acid and flavor are added. The melt is cooled to 65–70° C. in a tapered roller.

2. Filling

Recipe

| Raftilose L95 (fructooligosaccharide) | 2.5 kg |
|---|---|
| 1,6-GPS-enriched mixture (82% 1,6-GPS, 18% 1,1-GPM) | 5.9 kg |
| Water | 1.5 kg |
| Citric acid | 0.09 kg |
| Lemon flavor | 0.01 kg |

Production

Raftilose L95 is heated to 80° C. with water; a finely pulverized 1,6-GPS-enriched mixture is dissolved therein; after cooling to 70° C., acid and flavor are added and processed into the plastic melt from the 1,1-GPM-enriched mixture as a filling in the tapered roller. The filling is approximately 10–15% of the total candy mass.

The coating of the filled hard caramel is stable with respect to atmospheric water intake (good storage behavior); the filling is liquid and because it lacks maltitol syrup, suitable for diabetics.

Example 11

Production of Coated Soft Caramels, wherein the Coating Contains 1,1-GPM-enriched Mixture and the Core, 1,6-GPS-enriched Mixture The recipe for the soft caramel core corresponds to the recipe as described in Example 7.

The recipe for the dragee coating corresponds to the mixture indicated in Example 3.

The obtained coated soft caramels exhibit an increased storage stability and are suitable for diabetics.

Example 12

Replacement of Readily Soluble Sugar Substitutes by a 1,6-GPS-enriched Mixture in Chocolate, in Particular, Calorie-reduced Chocolate Chocolate Recipe of the Mixture

|   | Bitter chocolate | Milk chocolate |
|---|---|---|
| Cocoa mass | 45 kg | 11 kg |
| 1,6-GPS-enriched mixture (82% 1,6-GPS, 18% 1,1-GPM) | 44 kg | 39 kg |
| Hazelnut paste | 3 kg | 3 kg |
| Whole milk powder | — | 26 kg |
| Cocoa butter | — | 17 kg |
| Sweeteners | 0.1 kg | 0.1 kg |

Recipe of the Conching Mass

|   | Bitter chocolate | Milk Chocolate |
|---|---|---|
| Chocolate mixture | 92.1 kg | 96.1 kg |
| Cocoa butter | 7.0 kg | 3.0 kg |
| Lecithin | 0.5 kg | 0.5 kg |
| Flavor 1 | 0.4 kg | 0.3 kg |
| Flavor 2 | — | 0.1 kg |

Process Technical Data

| Process parameters | Bitter chocolate | Milk chocolate |
|---|---|---|
| Mixing time (min) | ca. 5 | ca. 10 |
| Temperature after the mixing | ca 37° C. | ca 37° C. |
| Roller performance, kg/h-preliminary rolling, according to slit width and length of the roller | 1200–1900 | 1200–1900 |
| Roller performance, kg/h-fine rolling (1000 mm in length) | 280-300 | 280-300 |
| Conching temperature | max. 70° C. | max. 60° C. |
| Conching time (h) | 24 | 24 |

Of course, the 1,6-GPS-enriched mixture is also suitable for the production of calorie-reduced chocolate, in which fat substitutes, such as inulin or polydextrose, are used. Chocolates can be produced which have less than 31%, preferably less than 30%, and particularly preferably, less than 29% fat content.

The use of 1,6-GPS-enriched mixture makes it possible to increase the conching temperature clearly, in comparison to the traditional raw materials, due to the low content of water of hydration (<1%). Improved flow characteristics of the chocolate masses during the processing are produced. The 1,6-GPS-enriched mixture in accordance with the invention, therefore, makes it possible to provide an improved method for the production of chocolate.

Example 13

Sensory Analysis of the Sweetening Power of 1,1-GPM- or 1,6-GPS-enriched 1,1-GPM/1,6-GPS Mixtures For the analysis of the sweetening power, a mixture with a ratio of 1,1-GPM/1,6-GPS of 6.79:1 was used as the 1,1-GPM-enriched mixture. A mixture with a ratio of 1,6-GPS/1,1-GPM of 4.51:1 was used as the 1,6-GPS-enriched mixture.

The mixtures were given to the test persons in the form of aqueous solutions.
Threshold Value Determination:
Concentration Series 1 (1,1-GPM) of the Threshold Test

TABLE II

| Sample characterization | Concentration (g/100 g) | Recognition of the threshold value (%) |
|---|---|---|
| 220895/1 | 0 | 0 |
| 220895/2 | 2 | 57.14 |
| 220895/3 | 4 | 14.28 |
| 220895/B | 5 | 28.57 |
| 220895/4 | 6 | 0 |

Concentration Series 2 (1,6-GPS) of the Threshold Test

TABLE III

| Sample characterization | Concentration (g/100 g) | Recognition of the threshold value (%) |
|---|---|---|
| 220895/5 | 0 | 0 |
| 220895/6 | 2 | 71.43 |
| 220895/7 | 4 | 14.28 |
| 220895/A | 5 | 14.28 |
| 220895/B | 6 | 0 |

When using a 1,6-GPS-enriched mixture, a low sugar alcohol concentration is recognized sooner, than when using a 1,1-GPM-enriched mixture.
Differentiation Test In the differentiation test in pairs (duo test), it was revealed that 62.5% (5 of 8 test persons) perceived the 1,6-GPS-rich mixture in a 10% concentration as sweeter and 37.5% (3 of 8 test persons), the 1,1-GPM-rich mixture.

Example 14

Production and Investigation of Hard Caramels in Accordance with the Invention

For the production of various hard caramels, hydrogenated isomaltulose (1) (ISMOALT$^R$) and mixtures (2)–(7), in accordance with the invention and as listed in Table IV, were used as raw materials (DS: dry substance).

TABLE IV

| Raw Material Designation | 1,1-GPM fraction (% DS) | 1,6-GPS fraction (% DS) |
|---|---|---|
| Isomalt$^R$ (1) | 48.6 | 50.3 |
| Isomalt PU-3, 3/55-F (2) | 2 | 71.43 |
| Isomalt PU-1, 9/45-F (3) | 23.1 | 75.1 |
| Isomalt PU-1, 35-F (4) | 32.8 | 65.6 |
| Isomalt Pu-3, 3/tt-FK (5) | 60.7 | 38.3 |
| Isomalt PU-1, 9/45-FK (6) | 72.4 | 26.8 |
| Isomalt PU-1/35-FK (7) | 83.2 | 16.4 |

Key:
1 Raw material designation
2 1,1-GPM fraction (% DS)
3 1,6-GPS fraction (% DS)

The caramels were stored for different periods of time at 70% relative humidity at 25° C. (water content of the caramels: 1.5%).

Figure 10:
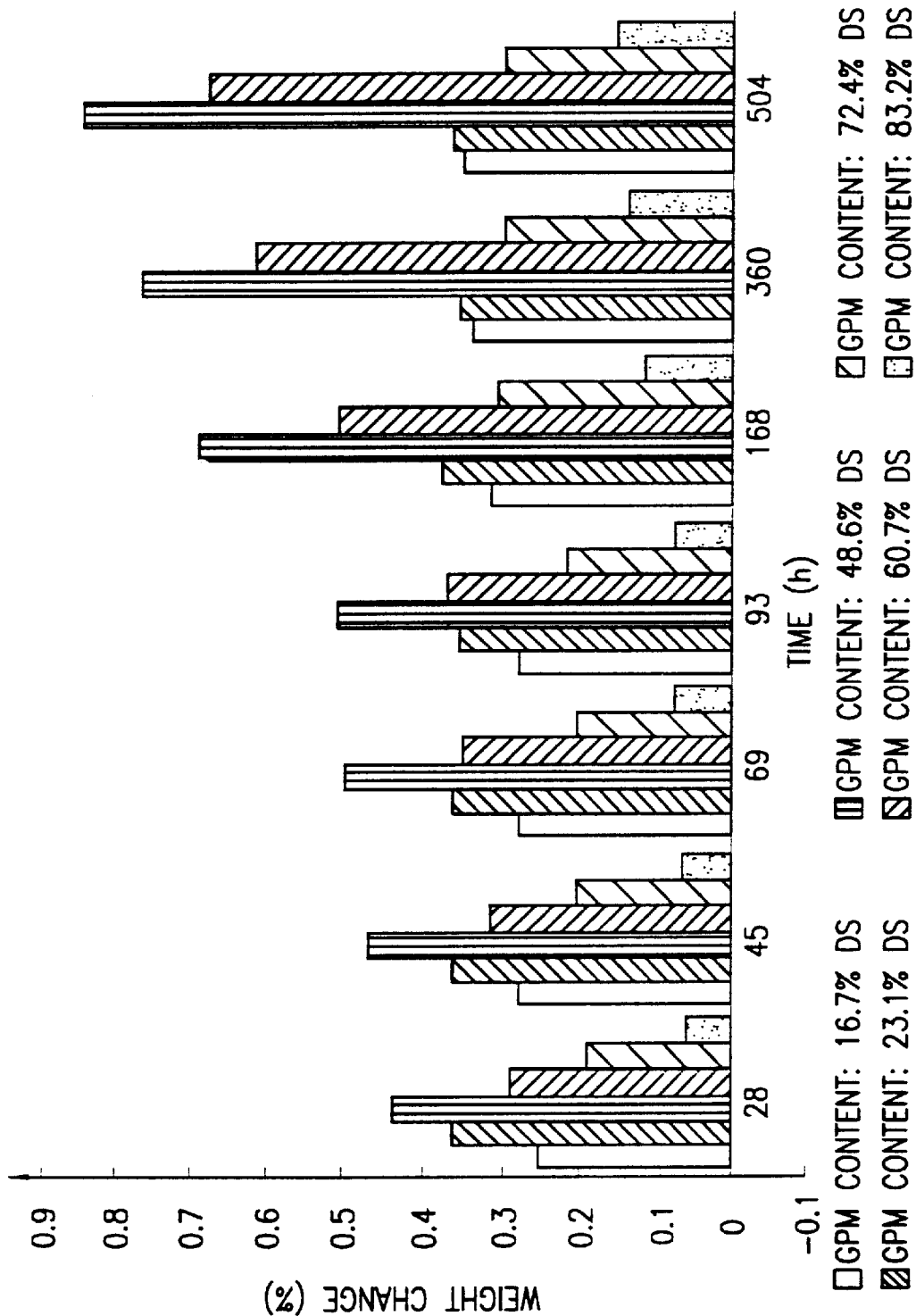
FIG. 10 represents the dependence of the weight change of hard caramels on their composition of 1,6-GPS and 1,1-GPM.

FIG. 10 shows that the hard caramels from traditional hydrogenated isomaltulose exhibit a considerably increased water intake in the storage test, in comparison to the products in accordance with the invention. The caramels in accordance with the invention, therefore, have a considerably better storage capacity.

What is claimed is:

1. A compressed material selected from the group consisting of a mixture consisting of 1,6-GPS (6O-α-D-glucopyranosyl-D-sorbitol) and 1,1-GPM (1-O-α-D-glucopyranosyl-D-mannitol) in a ratio of 57:43 wt % to 99:1 wt % and a mixture consisting of 1,6-GPS and 1,1-GPM in a ratio of 1:99 wt % to 43:57 wt %.

2. A compressed material according to claim 1 containing gelatin, fat or fat substitutes.

3. A compressed material according to claim 2 which contains intensive sweeteners selected from the group consisting of cyclamate, saccharin, aspartame, glycyrrhizin, neohesperidin, dihydrochalcone, thaumatin, monellin, acesulfame, alitame and sucralose.

4. A compressed material according to claim 1 which contains intensive sweeteners selected from the group consisting of cyclamate, saccharin, aspartame, glycyrrhizin, neohesperidin, dihydrochalcone, thaumatin, monellin, acesulfame, alitame and sucralose.

* * * * *